United States Patent [19]

Chambon et al.

[11] Patent Number: 4,721,711
[45] Date of Patent: Jan. 26, 1988

[54] PYRIDAZINE DERIVATIVES ACTIVE ON THE CENTRAL NERVOUS SYSTEM, AND MEDICAMENTS IN WHICH THEY ARE PRESENT

[75] Inventors: Jean-Pierre Chambon, Montarnaud; Kathleen Biziere, Clapiers; Camille-Georges Wermuth, Strasbourg, all of France

[73] Assignee: Sanofi

[21] Appl. No.: 783,686

[22] Filed: Oct. 3, 1985

Related U.S. Application Data

[63] Continuation of Ser. No. 571,697, Jan. 18, 1984, abandoned.

[30] Foreign Application Priority Data

Jan. 27, 1983 [FR] France .................... 8301234

[51] Int. Cl.[4] ................ C07D 413/12; A61K 31/535
[52] U.S. Cl. .................... 514/247; 514/248; 544/224; 544/238; 544/239
[58] Field of Search .................... 544/224, 238, 239; 514/247, 252

[56] References Cited

U.S. PATENT DOCUMENTS

| | | | |
|---|---|---|---|
| 4,508,720 | 4/1985 | Kan et al. | 544/224 |
| 4,514,397 | 4/1985 | Wermuth et al. | 544/224 |
| 4,565,814 | 1/1986 | Kan et al. | 514/228 |
| 4,576,946 | 3/1986 | Wermuth et al. | 544/224 |

OTHER PUBLICATIONS

Chambon et al., *Proc. Natl. Acad. Sci. USA*, vol. 82, pp. 1832–1836, Mar. 1985.

Roberts et al., "Basic Principles of Organic Chemistry", p. 556.

Le Clerc et al., Eur. J. Med. Chem. 1976-11, No. 2, pp. 107 to 113.

*Primary Examiner*—Nicholas S. Rizzo
*Attorney, Agent, or Firm*—Bacon & Thomas

[57] ABSTRACT

The invention relates to the pyridazine derivatives of the formula:

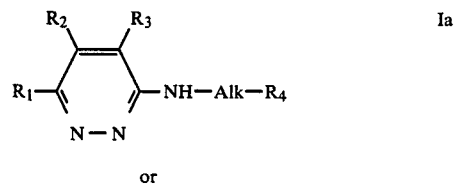

or

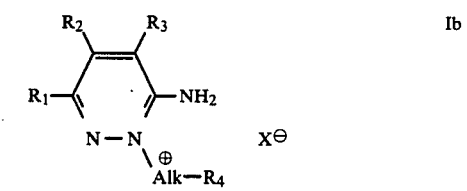

in which $R_1$ is H, a substituted or unsubstituted phenyl group, a naphthyl group, a cyclohexyl group, a thien-2-yl group, a thien-3-yl group or an indol-3-yl group, $R_2$ is H or an alkyl or phenyl group, $R_3$ is H, an alkyl, or phenyl group in formula Ib and a cyano group in formula Ia, and Alk is $(CH_2)_n$ where n is 2, 3 or 4, or —CH$_2$—C≡C—, and $X^-$ is halide, a process for the preparation of the said products and their application as medicaments.

21 Claims, No Drawings

PYRIDAZINE DERIVATIVES ACTIVE ON THE CENTRAL NERVOUS SYSTEM, AND MEDICAMENTS IN WHICH THEY ARE PRESENT

This application is a Rule 60 continuation of application Ser. No. 571,697, filed Jan. 18, 1984, now abandoned.

The present invention relates, by way of new products, to pyridazine derivatives.

It also relates to a process for the preparation of these compounds and the medicaments which contain at least one of said derivatives as the active principle.

The compounds according to the invention correspond to the general formulae:

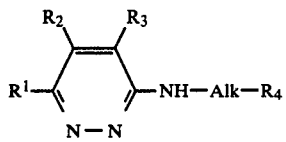

or its isomer

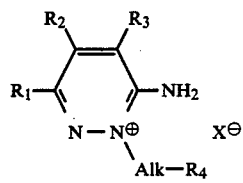

when
R$_3$ is other than cyano as defined below. In these formulae R$_1$ denotes hydrogen, a lower alkyl group, a phenyl group, a phenyl group monosubstituted by a halogen, a nitro group, a lower alkyl group, a lower alkoxy group, a hydroxyl group or a trifluoromethyl group, a phenyl group disubstituted by a halogen, a naphthyl group, a cyclohexyl group, a thien-2-yl group, a thien-3-yl group or an indol-3-yl group;

R$_2$ represents hydrogen, a lower alkyl group or a phenyl group;

R$_3$ represents hydrogen, a lower alkyl group, or a phenyl group in Formula Ib and a cyano group in Formula Ia above;

Alk represents a group (CH$_2$)$_n$, in which n is an integer equal to 2, 3 or 4, or a 1,2-propynyl group —CH$_2$—C≡C—; and R$_4$ represents:
—COOH
—COO-alkyl
—CONH$_2$
—C≡N; and X is a halide ion.

In the present Application, lower alkyl denotes an alkyl group having from 1 to 4 carbon atoms and lower alkoxy group denotes a lower O-alkyl group.

The compounds (I) are capable of giving additions salts with mineral or organic acids. The present invention also relates to the addition salts which the compounds (I) give with pharmaceutically acceptable acids.

The compounds according to the invention can be obtained from the appropriately substituted 3-chloropyridazines 1 according to the following reaction scheme:

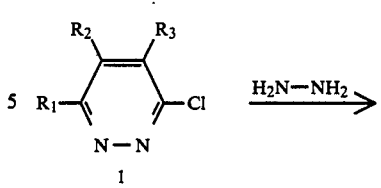

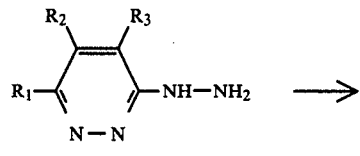

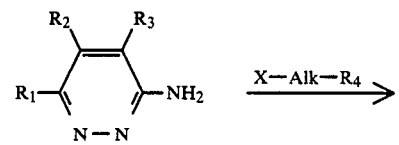

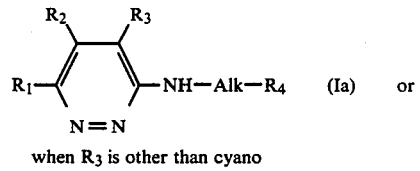

when R$_3$ is other than cyano

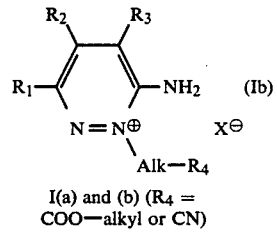

I(a) and (b) (R$_4$ = COO—alkyl or CN)

The pyridazines chlorinated in the 3-position are used as starting materials for preparing the corresponding 3-aminopyridazines 3. In practice, as direct conversion of the chlorinated derivatives to the amino derivatives is found to be impracticable, it is carried out via the hydrazine derivatives 2, which are obtained with good yields by heating the chlorinated derivatives 1 with excess hydrazine hydrate under reflux. On hydrogenation in the presence of a catalyst such as Raney nickel, the compounds 2 lead to the compounds 3.

Reaction of an ω-halogenoester X—Alk—R$_4$, in which X represents a halogen, preferably bromine, and R$_4$ represents a lower COO-alkyl group or the cyano group, with 3 gives the compounds Ia and Ib in which R$_4$ represents a lower COO-alkyl group or a cyano group. The reaction is carried out by heating the reactants in a solvent such as dimethylformamide, at a temperature of between 50° and 100° C.

The compounds Ia and Ib in which R$_4$ represents a —COOH group are obtained from the compounds in which R$_4$ represents a lower —COO-alkyl group by saponification in an acid medium, preferably by heating with a hydracid such as hydrochloric acid or hydrobromic acid, in acetic acid, at a temperature of between 20° and 100° C. The acid is isolated directly, in the form of the salt corresponding to the hydracid used, by evaporation to dryness.

Finally, the compounds Ia and Ib in which R$_4$ represents a carboxamido group can be prepared either from the corresponding esters Ia and Ib by reaction with a solution of ammonia in an aliphatic alcohol such as methanol, or from the nitriles Ia and Ib.

In the particular case where Alk represents an acetylenic group, the acids Ia and Ib are obtained by carbonating the pyridazine substituted in the 3-position by a group —NH—Alk in which alk is an acetylenic group.

The 3-chloropyridazines used as starting materials are known compounds or can be prepared by known processes, in particular by reacting excess phosphorus oxychloride with the corresponding 2H-pyridazin-3-ones.

The non-limiting examples which follow are given by way of illustration of the present invention.

EXAMPLE 1

3-Amino-2(3-ethoxycarbonylpropyl)-4-methyl-6-(naphth-1-yl)-pyridazinium chloride

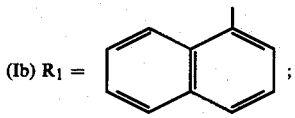

(Ib) $R_1 =$ ;

$R_2 = H$; $R_3 = CH_3$;
$Alk = (CH_2)_3$;
$R_4 = -COOC_2H_5$;
$X^- = Cl^-$ (a)-3-Hydrazino-4-methyl-6-(naphth-1-yl)-pyridazine A mixture of 6.0 g of 3-chloro-4-methyl-6-(naphth-1-yl)-pyridazine and 4.8 g of hydrazine hydrate is heated under reflux for 4 hours. On cooling, a precipitate forms, which is filtered off and washed with water. It is recrystallised from methanol. Melting point: 206° C.

(b)-3-Amino-4-methyl-6-(naphth-1-yl)-pyridazine 2 g of Raney nickel are added to a methanol solution of 5.0 g of the hydrazino derivative obtained above, and hydrogenation is carried out at ambient temperature under one atmosphere for 72 hours. The catalyst is filtered off and the solvent is then evaporated off to dryness in vacuo. The residue is recrystallised from methanol. Melting point: 110° C.

(c)-3-Amino-2-(3-ethoxycarbonylpropyl)-4-methyl-6-(naphth-1-yl)-2-pyridazinium chloride 1.18 g of the amino derivative of paragraph b) are dissolved in the minimum quantity of dimethylformamide, an 1.46 g of ethyl ω-bromobutyrate are then added. The mixture is heated at 80° C. for 3 hours. After cooling, it is diluted with water and rendered alkaline with 1N sodium hydroxide solution. Extraction is carried out with ethyl acetate and the organic phase is dried over magnesium sulphate. It is evaporated to dryness in vacuo. The oil residue is taken up in a small quantity of methanol, and hydrogen chloride is bubbled into the solution until the pH is acid. Anhydrous ether is added and the precipitate is filtered off. It is recrystallised from isopropanol. Melting point: 168° C.

EXAMPLES 2 to 23

The compounds (I) collated below in Table I are obtained by following the procedure indicated above, but by varying the starting 3-chloropyridazines and/or the corresponding halogenoesters.

TABLE I

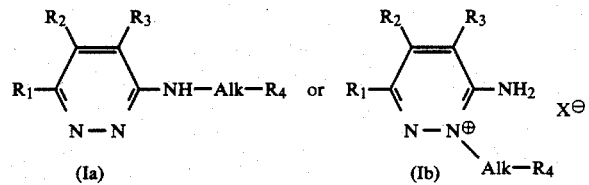

| Example No. | $R_1$ | $R_2$ | $R_3$ | Alk | $R_4$ | Base or salt $X^-$ or base Melting point °C. (solvent) |
|---|---|---|---|---|---|---|
| 2 | 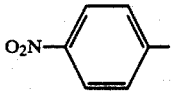 O$_2$N— | H | H | (CH$_2$)$_3$ | COOC$_2$H$_5$ | Br$^-$ 196 (95° Ethanol-Ether) |
| 3 | " | H | CH$_3$ | " | " | Br$^-$ (1) |
| 4 | 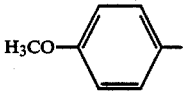 H$_3$CO— | H | CH$_3$ | " | " | Br$^-$ >250 (Dimethylformamide) |
| 5 | 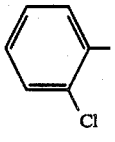 Cl | H | H | " | " | Br$^-$ 250 (Isopropanol) |
| 6 | " | H | CH$_3$ | " | " | Br$^-$ (1) |

TABLE I-continued $$\begin{matrix} R_1\text{—}C(=\text{N—N})\text{—C}(R_3)=C(R_2)\text{—NH—Alk—R}_4 & \text{or} & R_1\text{—C}(=\text{N—N}^{\oplus}(\text{Alk—R}_4))\text{—C}(R_3)=C(R_2)\text{—NH}_2 \quad X^{\ominus} \\ (Ia) & & (Ib) \end{matrix}$$

| Example No. | $R_1$ | $R_2$ | $R_3$ | Alk | $R_4$ | Base or salt $X^-$ or base Melting point °C. (solvent) |
|---|---|---|---|---|---|---|
| 7 | 2,4-dichlorophenyl | H | H | " | " | Br⁻ 220 (Isopropanol) |
| 8 | 4-chlorophenyl | H | H | " | " | Br⁻ 250 (Precipitate) |
| 9 | phenyl | CH₃ | H | " | " | Br⁻ 140 (Ethyl acetate) |
| 10 | 3-chlorophenyl | H | CH₃ | " | " | Br⁻ (1) |
| 11 | 4-methylphenyl | H | CH₃ | " | " | Br⁻ 260 |
| 12 | phenyl | H | —CN | " | COOCH₃ | Base 152 (Chromatographed) |
| 13 | phenyl | H | phenyl | " | COOC₂H₅ | Cl⁻ 204 (Isopropanol ether) |
| 14 | phenyl | H | CH₃ | " | " | Cl⁻ 248 |
| 15 | phenyl | H | H | " | " | Cl⁻ 245 |
| 16 | " | H | CH₃ | (CH₂)₂ | " | Br⁻ (1) |
| 17 | " | H | CH₃ | (CH₂)₄ | " | Br⁻ (1) |
| 18 | cyclohexyl | H | H | (CH₂)₃ | " | Br⁻ 149 (Isopropanol ether) |

TABLE I-continued

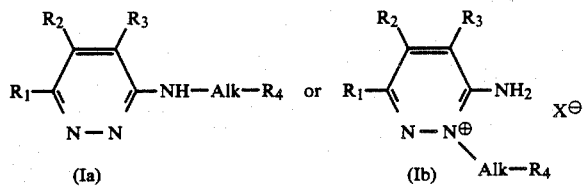

| Example No. | $R_1$ | $R_2$ | $R_3$ | Alk | $R_4$ | Base or salt $X^-$ or base Melting point °C. (solvent) |
|---|---|---|---|---|---|---|
| 19 | (2-thienyl) | H | H | " | " | Br⁻ 243 (Absolute ethanol) |
| 20 | (2-thienyl) | H | H | " | " | Br⁻ 250 (Precipitate) |
| 21 | CH₃ | (phenyl) | H | " | " | Br⁻ 174 (Isopropanol) |
| 22 | H | (phenyl) | H | " | " | Br⁻ (1) |
| 23 | (4-fluorophenyl) | H | H | " | " | Br⁻ (1) |

(1) used as such for saponification in an acid.

EXAMPLE 24

3-Amino-2-(3-carboxypropyl)-4-methyl-6-(naphth-1-yl)-2-pyridazinium chloride

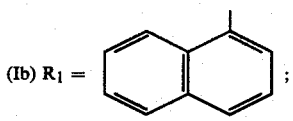

(Ib) $R_1 =$ naphth-1-yl;

$R_2 = H$; $R_3 = CH_3$
Alk = $(CH_2)_3$;
$R_4 = $ COOH;
$X^- = Cl^-$ 1.8 g of the ester obtained in Example 1 are dissolved in a mixture of 81 ml of acetic acid and 9 ml of concentrated hydrochloric acid. The mixture is heated at 100° C. for 9 hours and then evaporated to dryness in vacuo. The solid residue is recrystallised from isopropanol and gives the expected product.

Melting point: 260° C.

EXAMPLES 25 to 46

The acids (Ia) and (Ib) shown in Table II below are obtained, following the procedure of Example 24, from the various esters of Example 1.

TABLE II $$\text{(Ia)} \quad \underset{R_1}{\overset{R_2 \; R_3}{\diagdown}}\!\!\!\!\!\!\!\!\!\!\!\!\!\!\!\!\!\!\!\!\!\!-\text{NH—Alk—COOH} \quad \text{or} \quad \underset{R_1}{\overset{R_2 \; R_3}{\diagdown}}\!\!\!\!\!\!\!\!\!\!\!\!\!\!\!\!\!\!\!\!\!\!-\overset{\text{NH}_2}{\underset{\text{Alk—COOH}}{\text{N}=\overset{\oplus}{\text{N}}}}\; X^{\ominus} \quad \text{(Ib)}$$

| Example No. | $R_1$ | $R_2$ | $R_3$ | Alk | Melting point (°C.) (solvent) |
|---|---|---|---|---|---|
| 25 | $O_2N$—C$_6$H$_4$— | H | H | $(CH_2)_3$ | Br$^-$ 204 (Ethanol-Ether) |
| 26 | " | H | CH$_3$ | " | Cl$^-$ 258 |
| 27 | H$_3$CO—C$_6$H$_4$— | H | CH$_3$ | " | Br$^-$ 255 (Precipitate) |
| 28 | 2-Cl-C$_6$H$_4$— | H | H | " | Br$^-$ 226 (Isopropanol) |
| 29 | " | H | CH$_3$ | " | Cl$^-$ 0.5 H$_2$O 221 (Ethanol-Ether) |
| 30 | 2,4-Cl$_2$-C$_6$H$_3$— | H | H | " | Cl$^-$ >260 |
| 31 | 4-Cl-C$_6$H$_4$— | H | H | " | Br$^-$ 250 (Isopropanol-Water) |
| 32 | C$_6$H$_5$— | CH$_3$ | H | " | Br$^-$ 0.25 H$_2$O 165 (Isopropanol-Isopropyl ether) |
| 33 | 3-Cl-C$_6$H$_4$— | H | CH$_3$ | " | Br$^-$ 235 (Precipitate) |
| 34 | H$_3$C—C$_6$H$_4$— | H | CH$_3$ | " | Br$^-$ 264 (Isopropanol-Water) |
| 35 | C$_6$H$_5$— | H | CN | " | Hydrochloride 0.5 H$_2$O (Precipitate) |
| 36 | " | H | C$_6$H$_5$— | " | Cl$^-$ 204 (Isopropanol-Ether) |

TABLE II-continued (Ia) R₁–C(R₂)=C(R₃)–C(NH—Alk—COOH)=N–N= or (Ib) R₁–C(R₂)=C(R₃)–C(NH₂)=N–N⁺(Alk—COOH) X⁻

| Example No. | R₁ | R₂ | R₃ | Alk | Melting point (°C.) (solvent) |
|---|---|---|---|---|---|
| 37 | " | H | CH₃ | " | Cl⁻ 238 (Acetic acid-Ether) |
| 38 | " | H | H | " | Cl⁻ 240 |
| 39 | " | H | CH₃ | (CH₂)₂ | Br⁻ 210 (Acetic acid-Ether) |
| 40 | " | H | CH₃ | (CH₂)₄ | Cl⁻ 236 |
| 41 | cyclohexyl | H | H | (CH₂)₃ | Br⁻ 170 (Isopropanol-Ether) |
| 42 | 2-methylthienyl | H | H | " | Br⁻ 252 (95° Ethanol-Ether) |
| 43 | thienyl | H | H | " | Br⁻ 228 (Isopropanol-Water) |
| 44 | CH₃ | phenyl | H | " | Br⁻ 186 (Isopropanol-Ether) |
| 45 | H | phenyl | H | " | Cl⁻ 238 |
| 46 | 4-fluorophenyl | H | H | " | Cl⁻ 240 |

EXAMPLE 47

3-Amino-2-(3-carboxypropyl)-4-methyl-6-(4-hydroxyphenyl)-2-pyridazinium bromide

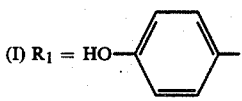

(I) R₁ = HO—C₆H₄—
R₂ = H; R₃ = CH₃
Alk = (CH₂)₃
R₄ = COOH
X⁻ = Br⁻;

A solution of 2 g of the acid of Example 30 in 20 ml of 48% hydrobromic acid is heated under reflux for 15 hours. After cooling, the solid which has formed is filtered off and washed with isopropanol and then with ether.

The solid is dried at 70° C. in vacuo to give 2 g of the expected product.

Melting point >260° C.

EXAMPLE 48

3-Amino-2-(3-carboxyprop-2-ynyl)-4-methyl-6-phenyl-2-pyridazinium chloride

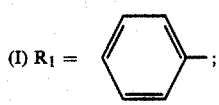

(I) R₁ = phenyl;
R₂ = H; R₃ = CH₃;
Alk = —CH₂C≡C—
R₄ = —COOH
X⁻ = Cl⁻;

4-Methyl-6-phenyl-3-(prop-2-ynylamino)-pyridazine is prepared by heating 7 g of 3-amino-4-methyl-6-phenyl-pyridazinium and 9 ml of propargyl bromide at 60° C. for 2 hours. After evaporation of the excess propargyl bromide, the residue is taken up in 300 ml of anhydrous benzene, and 1.77 g of sodium are added. The mixture is heated under reflux for 15 hours and the solution is then poured into excess solid carbon dioxide and left in contact therewith for several hours.

The solvent is evaporated off, the residue is taken up in isopropanol and a stream of hydrogen chloride is passed in. The solid is filtered off and recrystallised twice from isopropanol. Melting point: 101° C.

EXAMPLE 49

3-Amino-2-(3-cyanopropyl)-4,6-diphenylpyridazinium bromide

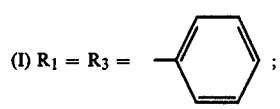

(I) $R_1 = R_3 = $ ;

$R_2 = H$;
Alk $= (CH_2)_3$
$R_4 = C\equiv N$;
$X^- = Br^-$ 2.47 g of 3-amino-4,6-diphenylpyridazine are dissolved in 5 ml of dimethylformamide, and 1.63 g of 4-bromobutyronitrile are added. The mixture is heated at 60° C. for 2 hours and left to cool. The crystals formed are filtered off and recrystallised from isopropanol. Melting point=202°-204° C.

EXAMPLES 51 and 52

The compounds below are obtained in the same manner by following the same procedure, but by varying the starting 3-aminopyridazine: -3-amino-2-(3-cyanopropyl)-4-methyl-6-phenyl-2-pyridazinium bromide. Melting point >265° C. -3-amino-3-(3-cyanopropyl)-6-phenyl-2-pyridazinium bromide. Melting point: 262°-264° C.

EXAMPLE 52

3-Amino-2-(3-carboxamidopropyl)-4-methyl-6-phenyl-2-pyridazinium chloride

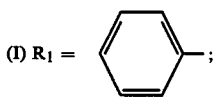

(I) $R_1 = $ ;

$R_2 = H$; $R_3 = CH_3$
Alk $= (CH_2)_3$
$R_4 = CONH_2$;
$X^- = Cl^-$ 3.33 g of the hydrobromide of the nitrile of Example 51 are dissolved in 100 ml of dry formic acid, and a stream of dry hydrogen chloride is then bubbled into the solution for 4 hours at a rate of about 5 liters/hour, with stirring. The mixture is evaporated to dryness in vacuo by heating as little as possible. The residue is taken up in ethanol, and anhydrous ether is added. The crystals are residue is taken up in ethanol, and anhydrous ether is added. The crystals are filtered off and recrystallised from isopropanol. Melting point: 130°-132° C.

The products according to the invention were studied for their activity on the central nervous system. Activity on the displacement of Y-aminobutyric acid from its post-synaptic receptor.

Method:

The neurochemical activity of the derivatives of the present invention on the GABA-ergic system was evaluated by measuring the displacement of Y-aminobutyric acid (GABA) from its post-synaptic receptor.

The study was carried out by the method of ENNA and SNYDER (Brain Res. 100, 81-97, 1975).

The displacement experiment was carried out in vitro in the presence of a suspension of synaptic membranes and tritiated GABA at a final concentration of 3.6 nM.

Results:

| Product of Example No. | Median effective concentration ($EC_{50}$) for displacement of tritiated GABA, in $\mu m$ |
| --- | --- |
| 37 | 2.8 |
| 38 | 1.34 |
| 24 | 2.9 |
| 39 | 10 |
| 33 | 0.70 |
| 31 | 1.25 |
| 27 | 5.0 |
| 42 | 2.4 |
| 41 | 10.5 |
| 47 | 3.0 |
| 43 | 0.83 |
| 30 | 7.0 |
| 29 | 3.2 |
| 34 | 0.71 |

Remarks:

The products of the invention have the ability to displace GABA from its synaptic receptor.

This in vitro study was complemented by an in vivo study.

The following tests were used.

1. Activity on the motility of mice

Method:

The tranquillising-sedative activity of the derivatives of the present invention was evaluated by measuring the spontaneous motility of mice by means of the activity test (J. R. BOISSIER and P. SIMON, Arch. Int. Pharmacodyn. 1965, 158, 212-221).

The equipment consisted of activity cages of the Apelab type (length=26 cm; width=21.5 cm; height=10 cm), through which two rays of light pass, acting on a photoelectric cell.

The animals were placed individually in the cages 45 minutes after oral administration of the product: each crossing of a light beam was counted by an individual counter. The scores corresponding to the movements of the animals were recorded for 10 minutes. The batches consisted of 12 mice per dose.

2. Effect on the antagonism of reserpine-induced ptosis

Method:

The antidepressive activity of the compounds was evaluated in the test for the antagonism of reserpine-induced ptosis in mice.

This study was carried out on batches of 10 female mice weighing 20±1 g. The products were administered intraperitoneally at the same time as the reserpine (2 mg/kg, administered intravenously). The mice were observed individually 1 hour after the administrations. The animals which did not exhibit ptosis during the 15 seconds of the observation were considered as antagonised. All the control animals, who had only received the vehicle and the reserpine, exhibited ptosis. The median effective dose for antagonism ($ED_{50}$) was evaluated by the probit method.

3. Effect on the rotational behaviour of mice after unilateral lesion of the nigro-striated passage by 6-(OH)-dopamine

Method:

The influence of the derivatives of the present invention on the central dopaminergic system was evaluated on the rotational behaviour of mice after unilateral lesion of the nigro-striated passage by 6-(OH)-dopamine. (P. PROTAIS and J. COSTENTIN, J. Pharmacol. 7(2), 251-255, 1976).

CD1 Charles River female mice, weighing 20 to 24 g, have previously undergone unilateral lesion of the striatum by the stereotaxic injection of 6-(OH)-dopamine at a dose of 8 μg per animal. One week after this operation, the product to be studied was administered intraperitoneally to grouos of 7 mice. The number of rotations was evaluated over 2 minutes, 1 hour after the administration of the product. The rotations on the same side as the lesion were counted as positive and those on the opposite side were counted as negative. The algebraic sum of the rotations for a group treated animals was compared with that for the group of control animals which had only received the vehicle (physiological serum).

The results obtained with one of the products representative of the invention, namely the product of Example No. 40, are shown in Table III below.

TABLE III

| Motility of the mice | | Antagonism of the reserpine-induced ptosis $ED_{50}$ mg/kg | Rotational behaviour of mice | |
|---|---|---|---|---|
| Dose in mg/kg | Effect | | Dose in mg/kg | Effect |
| 100 | −48%** | 29 | 0,5 | −50%** |
| 50 | −33%* | (26−32)* | 2 | −62%** |

*p 0.05
**p 0.01

The tests carried out in this way show that the products according to the invention act on the neuron by occupying the Y-aminobutyric acid receptor site. They have pharmacological properties in animals which make them suitable for use in human therapy for the treatment of neutrological or neuromuscular psychic complaints.

In particular, the products according to the invention can be used for humour or behaviour disorders such as depressive states, asthenia, Parkinson's disease, disturbances in eating habits, or insommia.

These products can be administered orally or by injection. The pharmaceutical compositions can be solid or liquid and can be presented, for example, in the form of tablets, gelatine capsules, granules, suppositories, or injectable preparations.

The dosage can vary within wide limits depending, in particular, on the type and seriousness of the complaint to be treated and according to the method of administration. When administered orally to adults, it is most frequently between 0.050 and 0.500 g per day, divided up into several individual doses if appropriate.

The following galenical preparation may be indicated as an example:

| Gelatine capsules | |
|---|---|
| Product of Example no. 40 | 100 mg |
| Aerosil | 0.5 mg |
| Magnesium stearate | 1.5 mg |
| STA RX 1500 starch | 40 mg |
| | 150 mg |

We claim:

1. A pyridazine compound having a formula:

$$R_1 \underset{N-N}{\overset{R_2 \quad R_3}{\diagdown}} NH-Alk-R_4 \quad (Ia)$$

in which:
$R_1$ denotes hydrogen, a lower alkyl group, a phenyl group, a phenyl group monosubstituted by a halogen, a nitro group, a lower alkyl group, a lower alkoxy group, a hydroxyl group or a trifluoromethyl group; a phenyl group disubstituted by halogen; a naphthyl group, a cyclohexyl group, a thien-2-yl group, a thien-3-yl group or an indol-3-yl group;

$R_2$ represents hydrogen, a lower alkyl group or a phenyl group;

$R_3$ represents a cyano group;

Alk represents a group $(CH_2)_n$, in which n is an integer equal to 2, 3 or 4, or a 1,2-propynyl group —$CH_2C \equiv C$—; and $R_4$ represents:
—COOH
—COO-alkyl
—CONH$_2$
—C≡N wherein alkyl is lower alkyl; and the addition salts of said derivatives with acids.

2. A compound according to claim 1, wherein $R_4$ is —COOH, —COO-alkyl or —CONH$_2$.

3. A compound according to claim 1, wherein $R_1$ is substituted or unsubstituted phenyl.

4. A compound according to claim 2 wherein $R_1$ is substituted or unsubstituted phenyl and Alk is $(CH_2)$ and $R_4$ is —COO-alkyl.

5. A compound according to claim 1, wherein $R_1$=phenyl, $R_2$=H, $R_3$=CN, Alk=$(CH_2)_3$ and $R_4$=COOCH$_3$.

6. A pyridazine compound having a formula $$R_1 \underset{\underset{Alk-R_4}{N-N_{\oplus}}}{\overset{R_2 \quad R_3}{\diagdown}} NH_2 \quad X^{\ominus} \quad (Ib)$$

in which:
$R_1$ denotes hydrogen, a lower alkyl group, a phenyl group, a phenyl group monosubstituted by a halogen, a nitro group, a lower alkyl group, a lower alkoxy group, a hydroxyl group or a trifluoromethyl group; a phenyl group disubstituted by halogen; a naphthyl group, a cyclohexyl group, a thien-2-yl group, a thien-3-yl group or an indol-3-yl group;

$R_2$ represents hydrogen, a lower alkyl group or a phenyl group;

$R_3$ represents hydrogen, a lower alkyl group, or a phenyl group;

Alk represents a group $(CH_2)_n$, in which n is an integer equal to 2, 3 or 4, or a 1,2-propynyl group $-CH_2C\equiv C-$; and $R_4$ represents:
- $-COOH$
- $-COO$-alkyl
- $-CONH_2$
- $-C\equiv N$ wherein alkyl is lower alkyl; and the addition salts of said derivatives with acids.

7. A compound according to claim 6, wherein $R_4$ is $-COOH$, $-COO$-alkyl or $-CONH_2$.

8. A compound according to claim 6, wherein $R_1$ is substituted or unsubstituted phenyl.

9. A compound according to claim 7, wherein $R_1$ is substituted or unsubstituted phenyl and Alk is $(CH_2)_3$ and $R_4$ is $-COO$-alkyl.

10. A compound according to claim 6, wherein $R_2=R_3=H$; Alk=$(CH_2)_3$; $R_4=-COOH$ or $-COO$-alkyl, alkyl being $CH_3$ or $C_2H_5$ and $R_1$ is selected from the group consisting of 4-nitrophenyl, 2-chlorophenyl, 2,4-dichlorophenyl, 4-chlorophenyl, phenyl, cyclohexyl, thien-2-yl, thien-3-yl and 4-fluorophenyl.

11. A compound according to claim 6, wherein $R_2=H$; $R_3=CH_3$; Alk=$(CH_2)_n$ with n=2, 3 or 4 or Alk is $-CH_2-C\equiv C-$; $R_4=-COOH$ or $-COO$-alkyl with alkyl=$CH_3$ or $C_2H_5$ and $R_1$ is selected from the group of 4-nitrophenyl, 4-methoxyphenyl, 2-chlorophenyl, naphthyl, phenyl, 4-methylphenyl and 4-hydroxyphenyl.

12. A compound according to claim 6, wherein $R_2=CH_3$, $R_3=H$, Alk=$(CH_2)_3$, $R_4=COOH$ or $COOC_2H_5$ and $R_1$ is phenyl.

13. A compound according to claim 6, wherein $R_2=H$, $R_3=H$ or $CH_3$; $R_4=-CONH_2$; Alk=$(CH_2)_3$ and $R_1$ is phenyl or 4-chlorophenyl.

14. A compound according to claim 6, wherein $R_4=CN$; $R_2=H$; Alk=$(CH_2)_3$ and $R_1=R_3=$phenyl.

15. A compound according to claim 6, wherein $R_1$ is

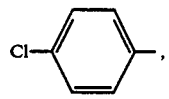

$R_2$ is H, $R_3$ is H, Alk is $(CH_2)_3$, and $R_4$ is $COOC_2H_5$.

16. A compound according to claim 6, wherein $R_1$ is

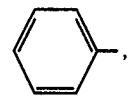

$R_2$ is H, $R_3$ is $CH_3$, Alk is $(CH_2)_3$ and $R_4$ is $COOC_2H_5$.

17. A compound according to claim 6, wherein $R_1$ is

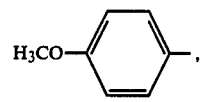

$R_2$ is H, $R_3$ is $CH_3$, Alk is $(CH_2)_3$ and $R_4$ is COOH.

18. A compound according to claim 6, wherein $R_1$ is

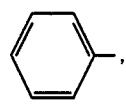

is H, $R_3$ is $CH_3$, Alk is $(CH_2)_3$ and $R_4$ is COOH.

19. A compound according to claim 6, wherein $R_1$ is

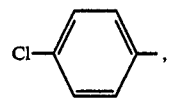

$R_2$ is H, $R_3$ is Alk is $(CH_2)_3$ and $R_4$ is $CONH_2$.

20. A pharmaceutical composition useful in human therapy for the treatment of neurological or neuromuscular psychic complaints containing an effective amount of the pyridazine compound according to claim 1.

21. A pharmaceutical composition useful in human therapy for the treatment of neurological or neuromuscular psychic complaints containing an effective amount of the pyridazine compound according to claim 6.

* * * * *